US011486878B2

(12) United States Patent
Crudgington et al.

(10) Patent No.: US 11,486,878 B2
(45) Date of Patent: Nov. 1, 2022

(54) COMPOSITIONS AND METHODS FOR IDENTIFYING CANCER CELLS

(71) Applicant: ZOMEDICA CORP., Ann Arbor, MI (US)

(72) Inventors: Allyson Crudgington, Ann Arbor, MI (US); Maria Dinkelmann, Ann Arbor, MI (US); Kevin Gorman, Ann Arbor, MI (US); Angy Guerrant, Ann Arbor, MI (US); Stephanie Morley, Ann Arbor, MI (US); Koen Verbrugghe, Ann Arbor, MI (US); Casey Wegner, Ann Arbor, MI (US)

(73) Assignee: ZOMEDICA CORP., Ann Arbor, MI (US)

( * ) Notice: Subject to any disclaimer, the term of this patent is extended or adjusted under 35 U.S.C. 154(b) by 630 days.

(21) Appl. No.: 16/409,408

(22) Filed: May 10, 2019

(65) Prior Publication Data
US 2019/0346448 A1 Nov. 14, 2019

Related U.S. Application Data

(60) Provisional application No. 62/669,555, filed on May 10, 2018.

(51) Int. Cl.
*G01N 33/543* (2006.01)
*G01N 33/574* (2006.01)
*G01N 33/569* (2006.01)

(52) U.S. Cl.
CPC ..... *G01N 33/57492* (2013.01); *G01N 33/543* (2013.01); *G01N 33/56972* (2013.01); *G01N 2469/10* (2013.01)

(58) Field of Classification Search
CPC ................... G01N 33/57492; G01N 33/56972
See application file for complete search history.

(56) References Cited

U.S. PATENT DOCUMENTS

| 9,404,864 | B2 | 8/2016 | Handique et al. | |
| 2001/0055776 | A1* | 12/2001 | Greenwalt | G01N 33/582 435/7.1 |
| 2014/0308669 | A1 | 10/2014 | Yang et al. | |
| 2016/0009812 | A1 | 1/2016 | Satelli et al. | |
| 2016/0077097 | A1 | 3/2016 | Rao et al. | |
| 2017/0101680 | A1 | 4/2017 | Kopf-Sill et al. | |
| 2019/0346448 | A1 | 11/2019 | Crudgington et al. | |
| 2020/0182877 | A1* | 6/2020 | Agopian | C07K 16/303 |

FOREIGN PATENT DOCUMENTS

| WO | WO 2017/218355 | 12/2017 |
| WO | WO 2018/105560 A1 | 6/2018 |

OTHER PUBLICATIONS

Satelli et al. Universal Marker and Detection Tool for Human Sarcoma Circulating Tumor Cells. Cancer Res. 74 (6): 1645-1650 (2014).*
Li et al. Cell-surface vimentive-positive macrophage-like circulating tumor cells as a novel biomarker of metastatic gastrointestinal stromal tumors. OncoImmunology 7 (5): e1420450 pp. 1-8 (published online Jan. 8, 2018).*
Yu et al. Comparative immunohistochemical characterization of canine seminomas and Sertoli cell tumors. J. Vet. Sci 10 (1): 1-7 (2009).*
Dill et al. Properties of Dog Blood. Journal of Biological Chemistry 95: 143-152 (Dec. 5, 1931).*
Adams, D.L., et al., Circulating giant macrophages as a potential biomarker of solid tumors. Proc Natl Acad Sci U S A. Mar. 4, 2014;111(9):3514-9.
Allard, et al., Tumor cells circulate in the peripheral blood of all major carcinomas but not in healthy subjects or patients with nonmalignant diseases. Clin Cancer Res. Oct. 15, 2004;10(20):6897-904.
Caniatti, M, et al., Canine Lymphoma: Immunocytochemical Analysis of Fine-needle Aspiration Biopsy. Vet Pathol. Mar. 1996;33(2):204-12.
Che, J, et al. Classification of large circulating tumor cells isolated with ultra-high throughput microfluidic Vortex technology. Oncotarget. Mar. 15, 2016;7(11):12748-60.
Chen, J-Y, et al. Sensitive and Specific Biomimetic Lipid Coated Microfluidics to Isolate Viable Circulating Tumor Cells and Microemboli for Cancer Detection. PLoS One. Mar. 3, 2016;11(3):e0149633.
Chudasama, D., et al., Perioperative detection of circulating tumour cells in patients with lung cancer. Oncol Lett. Aug. 2017;14(2):1281-1286.
Cobbold, et al., Monoclonal antibodies that define canine homologues of human CD antigens: Summary of the First International Canine Leukocyte Antigen Workshop (CLAW). Tissue Antigens. Mar. 1994;43(3):137-54.
Cristofanilli, et al., Circulating tumor cells, disease progression, and survival in metastatic breast cancer. N Engl J Med. Aug. 19, 2004;351(8):781-91.
Da Costa, A, et al. Identification of six potential markers for the detection of circulating canine mammary tumour cells in the peripheral blood identified by microarray analysis. J Comp Pathol. Feb.-Apr. 2012;146(2-3):143-51.
Da Costa, A, et al. Multiple RT-PCR markers for the detection of circulating tumour cells of metastatic canine mammary tumours. Vet J. Apr. 2013;196(1):34-9.
Da Costa, A, et al. Potential markers for detection of circulating canine mammary tumor cells in the peripheral blood. Vet J. Oct. 2011;190(1):165-8.
Danilenko, DM, et al. Canine leukocyte cell adhesion molecules (LeuCAMs): Characterization of the CD11/CD18 family. Tissue Antigens. Jul. 1992;40(1):13-21.

(Continued)

*Primary Examiner* — Gailene Gabel
(74) *Attorney, Agent, or Firm* — Casimir Jones, S.C.; Tanya A. Arenson (57) ABSTRACT

Provided herein are compositions and methods for identifying cancer cells. In particular, provided herein are optimized assays for identifying a variety of different cancer cells present in a sample at low concentrations.

14 Claims, 5 Drawing Sheets
(5 of 5 Drawing Sheet(s) Filed in Color)

(56) References Cited

OTHER PUBLICATIONS

ELISA Kit Catalog No. MBS1751068. Dog Canine Cadherin-2/N-Cadherin PicoKine, Jan. 15, 2018 [online], [Retrieved on Oct. 13, 2020], Retrieved from the Internet: <URL: https://www.mybiosource.com/cdh2-canine-elisa-kits/cadherin-2-n-cadherin/1751068>]; in entirety.
Gelain, ME, et al., CD44 in canine leukemia: Analysis of mRNA and protein expression in peripheral blood. Vet Immunol Immunopathol. May 15, 2014;159(1-2):91-6.
Gogoi, P, et al. Development of an Automated and Sensitive Microfluidic Device for Capturing and Characterizing Circulating Tumor Cells (CTCs) from Clinical Blood Samples. PLoS One. Jan. 25, 2016;11(1):e0147400.
Gonzalez-Fernandez, L, et al., Identification of Protein Tyrosine Phosphatases and Dual-Specificity Phosphatases in Mammalian Spermatozoa and Their Role in Sperm Motility and Protein Tyrosine Phosphorylation. Biol Reprod. Jun. 2009;80(6):1239-52.
Goto-Koshino, Y, et al., Differential expression of CD45 isoforms in canine leukocytes. Vet Immunol Immunopathol. Jul. 15, 2014;160(1-2):118-22.
Harb, W., et al., Mutational Analysis of Circulating Tumor Cells Using a Novel Microfluidic Collection Device and qPCR Assay. Transl Oncol. Oct. 1, 2013;6(5):528-38.
Henry, NL, et al., Cancer biomarkers. Mol Oncol. Apr. 2012;6(2):140-6.
Leader, M, et al., Vimentin: an evaluation of its role as a tumour marker. Histopathology. Jan. 1987;11(1):63-72.
Lee, JM, et al., The epithelial-mesenchymal transition: new insights in signaling, development, and disease. J Cell Biol. Mar. 27, 2006;172(7):973-81.
Meyer, A., et al., Multiple polymerase chain reaction markers for the differentiation of canine cutaneous peripheral nerve sheath tumours versus canine fibrosarcomas. J Comp Pathol. Feb.-Apr. 2014;150(2-3):198-203.
Mikolajczyk, SD, et al. Detection of EpCAM-Negative and Cytokeratin-Negative Circulating Tumor Cells in Peripheral Blood. J Oncol. 2011;2011:252361.
Pantel, K., et al.. Liquid biopsy: Potential and challenges. Mol Oncol. Mar. 2016;10(3):371-3.
Recombinant antibodies: highly reproducible with tailored specificity by Abcam (Apr. 22, 2018) [Retrieved from the Internet Oct. 14, 2020: <https://web.archive.org/web/20180422060756/https://www.abcam.com/primary-antibodies/recombinant-antibodies>].
Rutgen, BC, et al., A Saalmüller and I Schwendenwein. Composition of lymphocyte subpopulations in normal canine lymph nodes. Vet Clin Pathol. Mar. 2015;44(1):58-69.
Singh, A., et al., EMT, cancer stem cells and drug resistance: an emerging axis of evil in the war on cancer. Oncogene. Aug. 26, 2010;29(34):4741-51.
UniProt ID K7TRU2_MOUSE IgM heavy chain variable region, May 8, 2019 [online], [Retrieved on Nov. 24, 2020], Retrieved from the internet: <URL: https://www.uniprot.org/uniprot/K7TRU2.txt?verison-14>; in entirety, amino acids 89-104, 76.6% identity to SEQ ID No. 76.

* cited by examiner

FIG. 1

| Date and Sample | Block Dilution | Antibody Dilution | Percent Sensor Coupling Efficiency (all days)(%) | |
|---|---|---|---|---|
| 07/09/18 BGL 927 A | DW | DB | 96 | |
| 07/09/18 BGL 928 A | | | 97 | |
| 07/10/18 BGL 950 A | | | 99 | |
| 07/09/18 BGL 927 B | DW | DB | 100 | |
| 07/09/18 BGL 928 B | | | 99 | |
| 07/10/18 BGL 950 B | | | 99 | |
| 07/09/18 BGL 927 C | DW | DW | 92 | |
| 07/10/18 BGL 950 C | | | 95 | |
| 07/10/18 BGL 950 C | | | 89 | |
| 07/09/18 BGL 927 D | DB | DB | 94 | |
| 07/09/18 BGL 928 D | | | 93 | |
| 07/10/18 BGL 951 D | | | 95 | |

| Target | Antibody Clone | OSCA8 + | WBC - |
|---|---|---|---|
| N-cadherin | 8C11 | X | |
| N-cadherin | 13A9 | X | |
| N-cadherin | SP90 | X | |
| N-cadherin | SY02-46 | ✓ | X |
| c-kit | 371907 | X | |
| c-kit | R21-V | X | |
| c-kit | ST04-99 | X | |
| Nanog | 23D2-3C6 | X | |
| survivin | 1H5 | X | |
| survivin | 3F | X | |
| Zeb-1 | 3G6 | X | |
| FAPa | 427 | X | |
| vimentin (CSV) | 84-1 | ✓ | ✓ |
| vimentin | RM289 | ✓ | X |
| vimentin | SP20 | ✓ | X |

COMPOSITIONS AND METHODS FOR IDENTIFYING CANCER CELLS

This application claims priority to U.S. provisional patent application Ser. No. 62/669,555, filed May 10, 2018, which is incorporated herein by reference in its entirety.

FIELD OF THE DISCLOSURE

Provided herein are compositions and methods for identifying cancer cells. In particular, provided herein are optimized assays for identifying a variety of different cancer cells present in a sample at low concentrations.

BACKGROUND OF THE DISCLOSURE

Over the decades pets moved from the yard to the house to the bed, becoming more and more like another family member every year. Pet owners' willingness to spend money on extending the lives of these precious family members has also increased, but there is a cap to the cost most owners are willing to pay when their pet has been diagnosed with cancer. Veterinary medicine is a cash-based business and requires the ability of the veterinarian, who is the advocate for their patient that cannot speak for itself, to show true value for the medical dollars spent and often maximize on minimal budgets.

Current tools for diagnosing cancer in companion animals are costly because they may require significant capital investment at the point of care (e.g. imaging modalities like ultrasound), surgical biopsy including anesthesia, surgeon time and post-op recovery, or histopathologic examination of the biopsy sample. Moreover, tissue biopsies are plagued by limitations such as invasiveness, lack of procedure repeatability on a patient, and inadequate diagnostic performance. Another problem with the diagnostic process for cancer patients is many animals suffering from cancer are not stable enough for surgical biopsy.

The development of cancer liquid biopsy tests, non-invasive blood testing alternatives to surgical biopsies, is an area of intense focus in human medicine. Cancer liquid biopsy approaches that primarily leverage circulating tumor DNA/RNA (ctDNA and ctRNA) or CTCs are increasingly being developed for use in diagnostic work-ups and screening in human medicine. However, liquid biopsy offerings have yet to take hold in veterinary medicine. This is likely attributed to a number of factors including cost constraints and a still limited amount of veterinary focused research investigations. A small handful of veterinary companies have developed blood-based cancer tests that rely on approaches such as ELISAs for inflammatory markers and whole blood mRNA signature panels. But these blood tests do not have the necessary diagnostic utility to be used as liquid biopsy tests.

Additional liquid biopsy tests for veterinary applications are needed.

SUMMARY OF THE DISCLOSURE

Provided herein are compositions and methods for identifying cancer cells. In particular, provided herein are optimized assays for identifying a variety of different cancer cells present in a sample at low concentrations.

The present disclosure provides liquid biopsy assays that use circulating tumor cell (CTC) detection to allow for earlier diagnosis of malignant cancer using an easy to obtain sample (e.g., peripheral blood). The assays described herein provide clinical information for primary diagnoses, screening, monitoring, and staging/grading; this is done for a fraction of the cost of other diagnostic methods such as imaging and surgical biopsy. By reducing cost/time and improving the accuracy of diagnosis, as much money as possible is preserved to be used for earlier treatment thereby prolonging the lives of pets.

For example, in some embodiments, provided herein is a method of identifying the presence of cancer cells in a biological sample, comprising: a) isolating and capturing circulating tumor cells (CTC) from a biological sample; and b) detecting the presence of one or more cancer markers on the captured CTCs, wherein the one or more cancer markers comprise Vimentin (Vim) polypeptides (e.g., cell surface Vim). In some embodiments, the sample is blood, although other sample types are contemplated. The present disclosure is not limited to particular isolating, capturing, and detecting steps. Exemplary detection methodology using a microfluidic chip for capture and detection are described herein. In some embodiments, detecting comprises the use of first antibodies that specifically bind to Vim polypeptides. In some embodiments, the detecting is performed on the captured CTCs in the microfluidic chip. In some embodiments, the detecting comprises fluorescent microscopy to detect one or more fluorescently labelled secondary antibodies that bind to the first antibodies. In some embodiments, primary antibodies (e.g., labelled primary antibodies) are detected directly. In some embodiments, the method further comprises detecting the presence of captured white blood cells (WBCs). In some embodiments, the WBCs are identified by detecting the presence of a CD45 polypeptide on the captured WBC.

The present disclosure is not limited to particular sample preparation methods. In some embodiments, prior to the isolating and capturing step, the sample is prepared by a method comprising the steps of i) pre-fixing the sample in (e.g., approximately 0.01 to 0.8% (e.g., 0.4%) paraformaldehyde (PFA)); ii) diluting the pre-fixed sample in a buffer comprising buffered saline solution (e.g., Hank's and bovine serum albumin; iii) fixing the diluted sample in PFA (e.g., 2 to 5% (e.g., 4%) PFA); and iv) permeabilizing the fixed sample with a surfactant (e.g., Triton, e.g., 0.05 to 0.2% (e.g., 0.1%) Triton). In some embodiments, the sample is prepared in or on the microfluidic chip.

In some embodiments, a volume of 1 to 4 ml (e.g., 2 ml or less) of the blood sample is used. In some embodiments, a volume of 1 ml or more of each of the first antibodies is used. In some embodiments, one or more of the isolating, capture, and detecting are automated. In some embodiments, the sample is obtained from a non-human subject (e.g., a canine subject).

The present disclosure is not limited to detection of particular types of cancer. In some embodiments, the cancer comprises one or more of hemangiosarcoma, osteosarcoma, mammary cancers, mixed cancer tumors, or carcinomas. In some embodiments, the assay identifies the presence of any one (or more) of the cancers.

Additional embodiments provide a kit or system, comprising, in one or more containers: an antibody that specifically binds to a Vim polypeptide. In some embodiments, the kit or system further comprises a labelled secondary antibody (e.g., fluorescently labelled) that binds to the antibodies. In some embodiments, the kit or system further comprises an antibody to CD45.

Further embodiments provide a kit of system described herein for use in detecting the presence of cancer in a biological cancer.

Other embodiments provide a kit or system described herein for detecting the presence of cancer in a biological sample.

Additional embodiments are described herein.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 3 shows a flow cytometry experiment used to determine specificity of cancer marker antibodies. (A) Schematic for interpretation of double-labelled flow cytometry data. (B) Staining with anti-vimentin antibody clone SP20 and secondary antibody. (C) Staining with cell-surface vimentin antibody clone 84-1 and secondary antibody. (D) Staining with directly-conjugated 84-1 antibody.

DEFINITIONS

To facilitate an understanding of the present disclosure, a number of terms and phrases are defined below:

As used herein, the terms "detect", "detecting", or "detection" may describe either the general act of discovering or discerning or the specific observation of a composition.

The term "antibody" and "immunoglobulin" are used herein are used in the broadest sense and encompasses various antibody structures, including but not limited to monoclonal antibodies, polyclonal antibodies, multispecific antibodies (e.g. bispecific antibodies), and antibody fragments so long as they exhibit the desired antigen-binding activity. Also included are antibody fragments having an Fc region, and fusion proteins that comprise a region equivalent to the Fc region of an immunoglobulin.

An "antibody fragment" or "immunoglobulin fragment" are used interchangeably and refer to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$, single-chain antibody molecules (e.g. scFv), diabodies, and multispecific antibodies formed from antibody fragments.

The term "antigen binding domain" refers to the part of an antigen binding molecule (e.g., antigen binding protein) that comprises the area that specifically binds to and is complementary to part or all of an antigen. Where an antigen is large, an antigen binding molecule may only bind to a particular part of the antigen, which part is termed an epitope. An antigen binding domain may be provided by, for example, one or more antibody variable domains (also called antibody variable regions). Preferably, an antigen binding domain comprises an antibody light chain variable region (VL) and an antibody heavy chain variable region (VH). In some embodiments, an antigen binding domains comprise "complementarity determining regions" (CDRS) of the variable regions.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, β, δ, ε, γ, and μ.

The term "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; unnatural amino acids like p-aminophenylalanine, a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological activity may be found using computer programs, for example, DNAStar software. Variants can be tested in functional assays. Preferred variants have less than 10%, and preferably less than 5%, and still more preferably less than 2% changes (whether substitutions, deletions, and so on). For an amino acid substitution, the following nomenclature is used: Original amino acid, position, substituted amino acid.

The relatedness between two amino acid sequences or between two nucleotide sequences is described by the parameter "identity". For purposes of the present invention, the degree of identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends in Genetics 16: 276-277), preferably version 3.0.0 or later. The optional parameters 11644.000-EP7 used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows: (Identical Residues×100)/(Length of Alignment−Total Number of Gaps in Alignment).

The expression "amino acid position corresponding to" a position in a reference sequence and similar expression is intended to identify the amino acid residue that in the primary or spatial structure corresponds to the particular position in the reference sequence. The skilled person will appreciate that this can be done by aligning a given sequence with the reference sequence and identifying the amino acid residue that aligns with the particular position in the reference sequence.

The term "sample" as used herein is used in its broadest sense. In one sense it can refer to a tissue sample. In another sense, it is meant to include a specimen or culture obtained from any source, as well as biological. Biological samples may be obtained from animals (including humans) and encompass fluids, solids, tissues, and gases. Biological samples include, but are not limited to blood products, such as plasma, serum and the like. These examples are not to be construed as limiting the sample types applicable to the present disclosure.

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

DETAILED DESCRIPTION OF THE DISCLOSURE

Provided herein are compositions and methods for identifying cancer cells. In particular, provided herein are optimized assays for identifying a variety of different cancer cells present in a sample at low concentrations.

CTC technologies such as those described herein find use in cancer liquid biopsy testing in a variety of applications (e.g., veterinary medicine). CTCs are cancer cells that shed from a primary tumor into the bloodstream or lymphatic system. Technologies for CTC detection, enumeration and characterization thereby offer powerful clinical information for diagnosing and treating malignant tumors. For a CTC technology to be considered widely adequate for commercial diagnostic applications in the vet industry, the platform should 1) accurately enumerate CTCs using size-based capture of CTCs; 2) perform capture and analysis of CTCs using low cost consumables; 3) be able to provide results within 24 hrs of blood draw; and 4) offer automated, scalable capture and analysis that does not require sophisticated lab training. The assays described herein were extensively optimized to provide accurate detection of a variety of cancer types from a biological sample (e.g., blood). Exemplary compositions and methods are described herein.

I. Assays for Detection of Cancerous Cells

In some embodiments, the assays of the present disclosure comprise a first step of isolating CTCs from a biological sample (e.g., blood or other biological sample), followed by identification of tumor markers associated with the CTCs.

In some embodiments, the present disclosure utilizes cancer markers that identify a wide variety of cancers. Through experiments described herein, it was determined that cell surface vimentin was able to identify a variety of different types of cancer cells in a single assay. In some embodiments, the assays described herein detect the presence of one or more of hemangiosarcoma, osteosarcoma, mammary cancers, mixed cancer tumors and carcinomas.

The present disclosure is not limited to particular methods for capture and analysis of CTCs. In some embodiments, methods of the present disclosure utilize commercially available systems for isolation and/or characterization of CTCs. Examples include, but are not limited to, the CellSearch™ system, (Immunicon Corporation, Huntingdon Valley, Pa.) (Allard et al., Clin Cancer Res 2004; 10(20): 6897-904; Cristofanilli et al., N Engl J Med 2004; 351(8): 781-91; each of which is herein incorporated by reference in its entirety) and Celsee (Plymouth, Mich.) (Gogoi et al., 2016 and U.S. Pat. No. 9,404,864); each of which is herein incorporated by reference in its entirety.

The assays described herein are exemplified with the Celsee automated sample capture and analysis systems. However, the present disclosure is not limited to a particular method of isolating and/or analyzing CTCs. The Celsee system uses a microfluidic chip for sample capture and isolation (See e.g., FIG. 1), coupled to a fluorescence microscope for detection of cancer markers (e.g., via immunoassay).

In some embodiments, commercially available systems from Seraph or Qorvo (Greensboro, N.C.) are utilized.

In some embodiments, assays comprise the steps of preparing a sample, isolating the sample, and detecting the presence of cancer markers associated (e.g., on the surface or inside) the CTCs. In some embodiments, the presence of captured white blood cells is determined using antibodies to CD45. Such white blood cells are then excluded from further analysis. In some embodiments, automated sample preparation, capture, and analysis is performed. In some embodiments, software is used to identify captured CTCs that express the cancer markers described herein.

As described in Example 1, initial experiments resulted in clogging of samples in the instrument, poor detection of cancer cells, and high background/poor staining resolution. Provided herein are alternative protocols that were developed to allow non-human (e.g., canine) blood sample to works with the Celsee system.

Through experimentation, it was unexpectedly determined that a combination of marker selection and primary antibody selection (See e.g., Example 1); a sample preparation method of i) pre-fixing the sample in (e.g., approximately 0.01 to 0.8% (e.g., 0.4%) paraformaldehyde (PFA)); ii) diluting the pre-fixed sample in a buffer comprising buffered saline solution (e.g., Hank's and bovine serum albumin; iii) fixing the diluted sample in PFA (e.g., 2 to 5% (e.g., 4%) PFA); and iv) permeabilizing the fixed sample with a surfactant (e.g., Triton, e.g., 0.05 to 0.2% (e.g., 0.1%) Triton); a certain volume (e.g., 1 to 4 (e.g., 2) ml) of sample (e.g., blood sample); and a certain volume of primary antibody solutions (e.g., 1 ml) resulted in a robust assay able to detect cancer cells in a background of a complex sample and captured white blood cells.

The present disclosure is not limited to the particular volumes or concentrations of reagents and samples described herein. In some embodiments, + or −5%, 10%, 20%, 30%, 50%, 90%, etc. of the recited amounts or concentrations is specifically contemplated.

Additional methods for detecting protein markers associated with CTCs are described below. Examples include, but are not limited to, protein sequencing; and, immunoassays.

Illustrative non-limiting examples of protein sequencing techniques include, but are not limited to, mass spectrometry and Edman degradation.

Mass spectrometry can, in principle, sequence any size protein but becomes computationally more difficult as size increases. A protein is digested by an endoprotease, and the resulting solution is passed through a high pressure liquid chromatography column. At the end of this column, the solution is sprayed out of a narrow nozzle charged to a high positive potential into the mass spectrometer. The charge on the droplets causes them to fragment until only single ions remain. The peptides are then fragmented and the mass-charge ratios of the fragments measured. The mass spectrum is analyzed by computer and often compared against a database of previously sequenced proteins in order to determine the sequences of the fragments. The process is then repeated with a different digestion enzyme, and the overlaps in sequences are used to construct a sequence for the protein.

In the Edman degradation reaction, the peptide to be sequenced is adsorbed onto a solid surface (e.g., a glass fiber coated with polybrene). The Edman reagent, phenylisothiocyanate (PTC), is added to the adsorbed peptide, together with a mildly basic buffer solution of 12% trimethylamine, and reacts with the amine group of the N-terminal amino acid. The terminal amino acid derivative can then be selectively detached by the addition of anhydrous acid. The derivative isomerizes to give a substituted phenylthiohydantoin, which can be washed off and identified by chromatography, and the cycle can be repeated. The efficiency of each step is about 98%, which allows about 50 amino acids to be reliably determined.

Illustrative non-limiting examples of immunoassays include, but are not limited to: immunoprecipitation; Western blot; ELISA; immunohistochemistry; immunocytochemistry; flow cytometry; and, immuno-PCR. Polyclonal or monoclonal antibodies detectably labeled using various techniques known to those of ordinary skill in the art (e.g., colorimetric, fluorescent, chemiluminescent or radioactive) are suitable for use in the immunoassays.

Immunoprecipitation is the technique of precipitating an antigen out of solution using an antibody specific to that antigen. The process can be used to identify protein complexes present in cell extracts by targeting a protein believed to be in the complex. The complexes are brought out of solution by insoluble antibody-binding proteins isolated initially from bacteria, such as Protein A and Protein G. The antibodies can also be coupled to sepharose beads that can easily be isolated out of solution. After washing, the precipitate can be analyzed using mass spectrometry, Western blotting, or any number of other methods for identifying constituents in the complex.

A Western blot, or immunoblot, is a method to detect protein in a given sample of tissue homogenate or extract. It uses gel electrophoresis to separate denatured proteins by mass. The proteins are then transferred out of the gel and onto a membrane, typically polyvinyldiflroride or nitrocellulose, where they are probed using antibodies specific to the protein of interest. As a result, researchers can examine the amount of protein in a given sample and compare levels between several groups.

An ELISA, short for Enzyme-Linked ImmunoSorbent Assay, is a biochemical technique to detect the presence of an antibody or an antigen in a sample. It utilizes a minimum of two antibodies, one of which is specific to the antigen and the other of which is coupled to an enzyme. The second antibody will cause a chromogenic or fluorogenic substrate to produce a signal. Variations of ELISA include sandwich ELISA, competitive ELISA, and ELISPOT. Because the ELISA can be performed to evaluate either the presence of antigen or the presence of antibody in a sample, it is a useful tool both for determining serum antibody concentrations and also for detecting the presence of antigen.

Immunohistochemistry and immunocytochemistry refer to the process of localizing proteins in a tissue section or cell, respectively, via the principle of antigens in tissue or cells binding to their respective antibodies. Visualization is enabled by tagging the antibody with color producing or fluorescent tags. Typical examples of color tags include, but are not limited to, horseradish peroxidase and alkaline phosphatase. Typical examples of fluorophore tags include, but are not limited to, fluorescein isothiocyanate (FITC) or phycoerythrin (PE).

Flow cytometry is a technique for counting, examining and sorting microscopic particles suspended in a stream of fluid. It allows simultaneous multiparametric analysis of the physical and/or chemical characteristics of single cells flowing through an optical/electronic detection apparatus. A beam of light (e.g., a laser) of a single frequency or color is directed onto a hydrodynamically focused stream of fluid. A number of detectors are aimed at the point where the stream passes through the light beam; one in line with the light beam (Forward Scatter or FSC) and several perpendicular to it (Side Scatter (SSC) and one or more fluorescent detectors). Each suspended particle passing through the beam scatters the light in some way, and fluorescent chemicals in the particle may be excited into emitting light at a lower frequency than the light source. The combination of scattered and fluorescent light is picked up by the detectors, and by analyzing fluctuations in brightness at each detector, one for each fluorescent emission peak, it is possible to deduce various facts about the physical and chemical structure of each individual particle. FSC correlates with the cell volume and SSC correlates with the density or inner complexity of the particle (e.g., shape of the nucleus, the amount and type of cytoplasmic granules or the membrane roughness).

Immuno-polymerase chain reaction (IPCR) utilizes nucleic acid amplification techniques to increase signal generation in antibody-based immunoassays. Because no protein equivalence of PCR exists, that is, proteins cannot be replicated in the same manner that nucleic acid is replicated during PCR, the only way to increase detection sensitivity is by signal amplification. The target proteins are bound to antibodies which are directly or indirectly conjugated to oligonucleotides. Unbound antibodies are washed away and the remaining bound antibodies have their oligonucleotides amplified. Protein detection occurs via detection of amplified oligonucleotides using standard nucleic acid detection methods, including real-time methods.

In some embodiments, immunomagnetic detection is utilized. In some embodiments, detection is automated. Exemplary immunomagnetic detection methods include, but are not limited to, those commercially available from Veridex (Raritan, N.J.).

Further embodiments provide compositions, kits, and systems. Compositions for use in the diagnostic methods of the present disclosure include, but are not limited to, antibodies, detection reagents, and sample preparation reagents. Particularly preferred compositions detect the presence of level of expression of tumor markers in a CTC sample.

Any of these compositions, alone or in combination with other compositions of the present disclosure, may be provided in the form of a kit. In some embodiments, antibodies and reagents are provided in one or more containers. Kits may further comprise appropriate controls and/or detection reagents.

II. Uses

As described herein, the present disclosure provides compositions and methods for detecting cancer cells in a sample. Such methods find use in research, screening, and diagnostic applications.

In some embodiments, the assays find use in diagnostic methods for identifying cancer in a sample from a subject. In some embodiments, the subject is a non-human animal. In some embodiments, the non-human animal is a companion animal (e.g., dog, cat, etc.). The present disclosure is illustrated with canine samples. However, it is specifically contemplated that the described methods can be used to detect cancer cells in samples from other companion or non-companion animals.

In some embodiments, a computer-based analysis program is used to translate the raw data generated by the detection assay (e.g., the presence, absence, or amount of cancer marker) into data of predictive value for a clinician (e.g., presence of cancer). The clinician can access the predictive data using any suitable means. Thus, in some preferred embodiments, the present disclosure provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present disclosure contemplates any method capable of receiving, processing, and transmitting the information to and from laboratories conducting the assays, information provides, medical personal, and subjects. For example, in some embodiments of the present disclosure, a sample (e.g., blood sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained (e.g., by a veterinary nurse) and sent to the profiling center, or subjects or pet owners may collect the sample themselves (e.g., a urine sample) and directly send it to a profiling center. Once received by the profiling service, the sample is processed and a profile is produced (i.e., cancer marker data), specific for the diagnostic or prognostic information desired for the subject.

The profile data is then prepared in a format suitable for interpretation by a treating clinician. For example, rather than providing raw data, the prepared format may represent a diagnosis (e.g., presence of cancer) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some exemplary embodiments, the sample (e.g., blood sample) is first obtained at the point of care (e.g., by a veterinary nurse), placed in a suitable container (e.g., vacuum blood tube), labeled with a unique identifier, and then sent to a testing lab (e.g., reference lab) by any suitable method. In some embodiments, the testing lab performs the analysis (e.g., using an automated system described herein) and provided results to the point of care provider in any suitable format (e.g., using an electronic portal). In some embodiments, depending on the analysis method, further sample preparation is performed at the point of care or testing laboratory (centrifugation).

In some exemplary embodiments, the sample (e.g., stool or urine sample) is first obtained at the point of care (e.g., by a veterinary nurse), placed in a suitable container (e.g., cuvette), labeled with a unique identifier, and then sent to a testing lab (e.g., reference lab) by any suitable method. In some embodiments, the testing lab performs the analysis (e.g., using an automated system suitable for analysis of urine or stool samples) and provided results to the point of care provider in any suitable format (e.g., using an electronic portal).

In some embodiments, all of the analysis is performed at the point of care (e.g., using an automated analysis system).

In some embodiments, the subject or pet owner is able to directly access the data using the electronic communication system. The subject or pet owner may chose further intervention or counseling based on the results. In some embodiments, the data is used for research use. For example, the data may be used to further optimize the inclusion or elimination of markers as useful indicators of a particular condition or stage of disease.

EXPERIMENTAL

The following examples are provided to demonstrate and further illustrate certain embodiments of the present disclosure and are not to be construed as limiting the scope thereof.

Example 1

Materials and Methods
Sample Acquisition

All samples were from dogs. Blood samples from a mix of healthy dogs, dogs with confirmed cancer diagnosis (diagnosis confirmed by histopathology report) and normal blood spiked with canine cancer cells (OSCA-8, DD-1, D17, EFS or DH82 cell lines) grown in culture were used on the Celsee (Ann Arbor, Mich.) system. Normal healthy samples were from a mix of beagles from a research colony and more real-world samples from in-house animals and veterinary clinics. Cancer samples were acquired from a number of veterinary clinics. Hemangiosarcoma and Osteosarcoma (both mesenchymal tissue-derived) were the cancer types used to develop this assay.

Sample Preparation and Analysis

Samples were prepared for CTC counts as detailed below, using the Celsee System, which includes a prep instrument and an analyzer (Gogoi et al., 2016). For this work, a Celsee Prep400 instrument including the Celsee Tracker software Version 0.2.0-ruo-il-ce and a current Celsee Analyzer imaging station using Celsee Analyzer Software version 0.9.9.8.42 and 0.9.9.8.65 was used. The data described herein were obtained using default imaging settings prior.

Prior to loading onto the prep instrument, blood was collected in K2 EDTA tubes and shipped to the lab. Initial experiments utilized Celsee's protocol for human blood (Gogoi et al., 2016): 2 mL blood is prefixed in 2 mL of Celsee's Dilution buffer and 200 uL of 0.4% PFA (Celsee's Fixative reagent) is added. Sample is then incubated 10 minutes on a rocker at room temperature. After incubation 2 mL of Dilution and Wash (HBSS+BSA) buffer tops off the sample and then 6 mL of sample are loaded into the prep funnel, and the sample is then immediately processed on the Prep instrument. Variants of this protocol including removing or altering the concentration, makeup or volume of the prefix solution and/or the subsequent dilution buffer were performed as described in the results section below.

Figure 1:
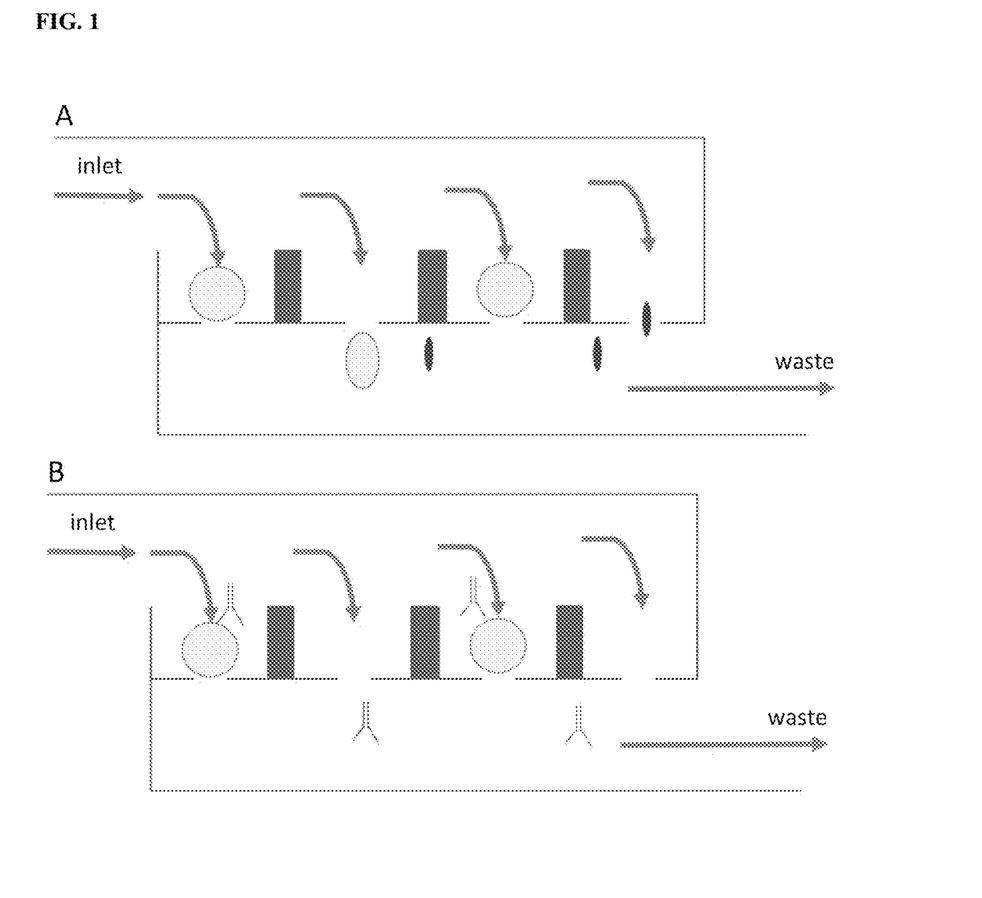
FIG. 1 shows a diagram of cell capture (A) and staining (B) in wells on a small section of the chip in a Celsee system.

The prep instrument (Gogoi et al., 2016) uses a pump to create a vacuum, which pulls fluid through small openings (7.5 μm by 8 μm) at the bottom of one of 56,320 wells aligned in multiple rows on a microfluidic chip. Circulating tumor cells and other larger cells (including some white blood cells) are trapped in the wells while smaller deformable cells (platelets, red blood cells, most white blood cells) pass through into a waste jar (FIG. 1A). The system then automatically draws additional fluids, dispensed from a pre-loaded cartridge, through the chip and incubates as appropriate to fix, permeabilize, stain and wash samples (FIG. 1B).

Results

Clogging of Samples

Figure 2:
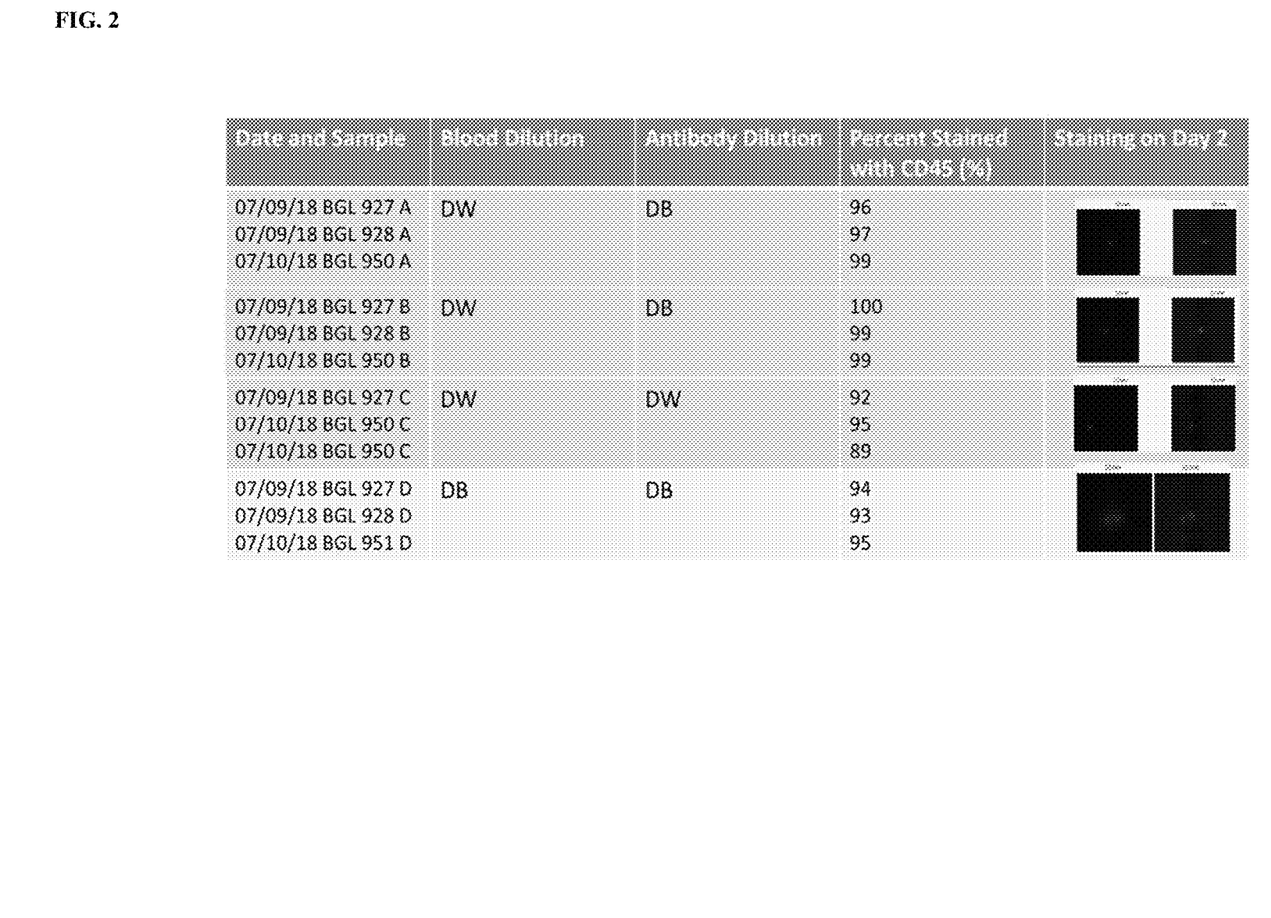
FIG. 2 shows optimization data for upstream sample processing in canine blood.

Initial experiments with dog blood on the Celsee instrument using the standard human blood protocol (0.4% PFA Prefix, 4% PFA fix, 0.1% Triton permeabilization), resulted in about half of the samples clogging the instrument. The samples could not complete processing because flow through the chip was blocked. This was not a problem with human samples. It was observed that samples that were not fixed did not clog. A number of variables were tested including fixative, blood collection tube type, blood dilution tube type, timing of pre-fixation and dilution buffer. It was found that using a different dilution buffer for pre-fixation (Dilution Wash buffer: HBSS+BSA) eliminated the problem (FIG. 2).

Marker Selection

The next step was to identify markers and associated staining conditions to optimize signal to noise while maintaining acceptable cell integrity and preventing clogging. In this assay setup, two markers were used: one to identify white blood cells captured by the chip, and a second to label circulating tumor cells.

The canonical WBC Marker used in many CTC applications is CD45 (Cobbold & Metcalfe 1994, Goto-Koshino et al. 2014). This marker is a large transmembrane protein with the internal portion of the protein highly conserved across species, and the external portion being more species-specific. Two commercially-available clones of anti-Canine CD45 monoclonal antibodies (Rat YKIX716.13 and Mouse CA12.10C12) that were raised against (and are likely specific to) canine CD45, and are used in canine assays (Cobbold & Metcalfe 1994, Caniatti et al. 1996), were identified.

Two antibodies raised to human CD45 that also recognize the protein from other species were tested: one used in the Celsee assay (F10-89-4) and one that has been used in flow cytometry on canine blood (clone 69, González-Fernandez et al. 2009). The two canine specific antibodies (Rat YKIX716.13 and Mouse CA12.10C12) gave detectable signal using the Celsee instruments while the two human antibodies did not. A marker to CD11a (HI111), an alternative marker of WBCs that identifies most but not all of the same populations of cells as CD45 (Danilenko et al. 1992. Rutgen et al. 2015) was also tested. This also did not give a detectable signal on the Celsee instruments.

Further testing was therefore conducted using the two canine specific antibodies. The rat antibody was preferred over the mouse clone as it resulted in better staining over a large set of samples.

Most clinical liquid biopsy tests in development are developed to identify specific cancer types (e.g. mammary, prostate, breast). To identify circulating tumor cells, protein markers specific to a given tissue type (e.g. epithelial or mesenchymal) are used. For example, the Cell Search platform uses epithelial markers EpCAM and Cytokeratin and has been validated to identify cancers of epithelial origin, such as prostate, colorectal, and breast cancers.

This example describes the development of a test for prevalent, difficult-to-biopsy canine cancers, for example, osteosarcoma and hemangiosarcoma. Both of these cancers are mesenchymal in origin, thus, a good marker of mesenchymal phenotype was identified.

Figure 3A:
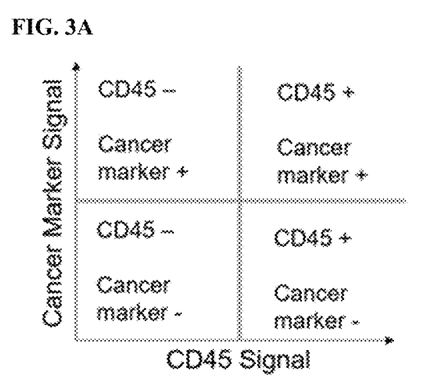
Figure 3B:
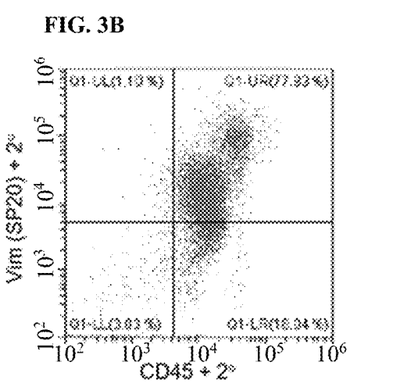
Figure 3C:
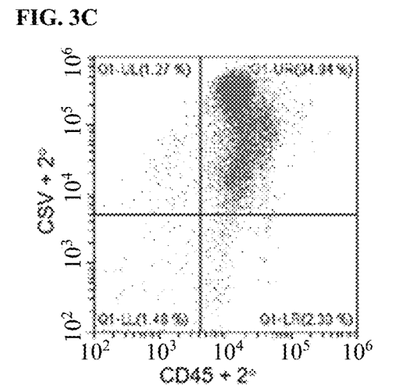

Initial assays tested the anti-vimentin antibody clone SP20. This antibody was not suitable for use in the assay. Vimentin exhibits significant staining on white blood cells (FIG. 3B); therefore any WBCs captured in the chip stained had a high likelihood of staining positive and, in instances where the CD45 staining was too weak, such a cell was falsely-scored as a CTC (Vim+/CD45−). Due to this phenomenon, the counts were artificially-high using blood samples from healthy patients.

Figure 3D:
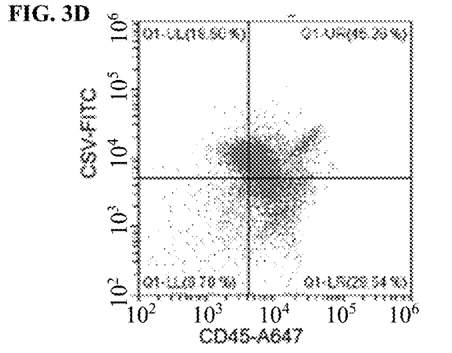
Figure 4:
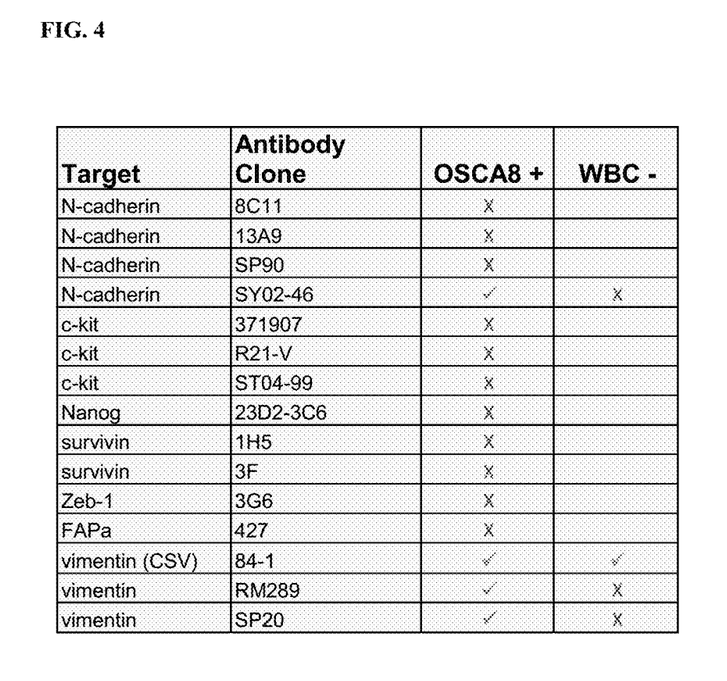
FIG. 4 shows the results of a systematic screen to identify candidate monoclonal antibodies for mesenchymal targets.

Further assays systematically tested many different targets and their associated antibodies to identify a cancer marker (FIG. 4). An antibody against the cell-surface domain of human vimentin (cell-surface vimentin, CSV), which is specifically expressed in mesenchymal CTCs in human cells, and importantly has low background staining in canine PBMCs when using the directly-conjugated antibody (FIG. 3D) was identified. Cell-surface vimentin (CSV) worked well as a cancer marker for both canine hemangiosarcoma and canine osteosarcoma cells spiked into canine blood devoid of CTCs, but only when used after permeabilization, indicating that the target may be a canine intracellular target. Thus, further assay development used CSV as the mesenchymal cancer marker.

CTC Detection Assay Development Summary

Figure 5:
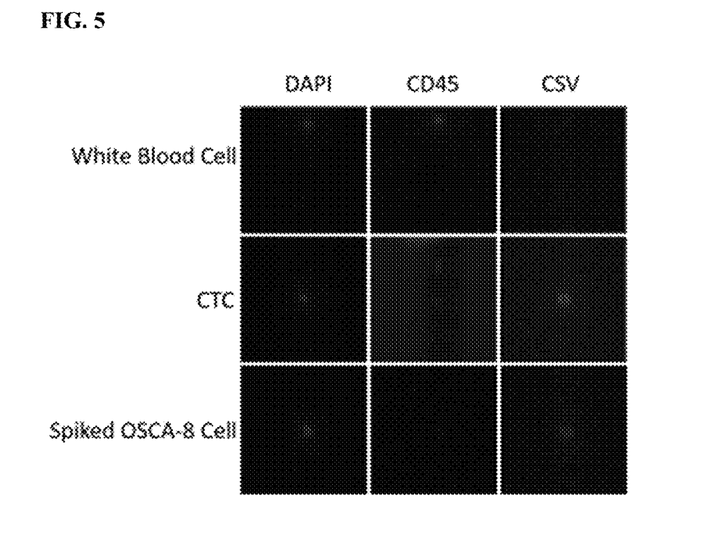
FIG. 5 shows representative images of a WBC, a CTC isolated from a cancer sample, and an OSCA-8 cell spiked into a normal sample using an exemplary assay described herein. Expected staining patterns for each of the cell types: CTCs/Spiked Cancer Cells: DAPI+, CD45−, CSV+; WBCs: DAPI+, CD45+, CSV−.
Figure 6:
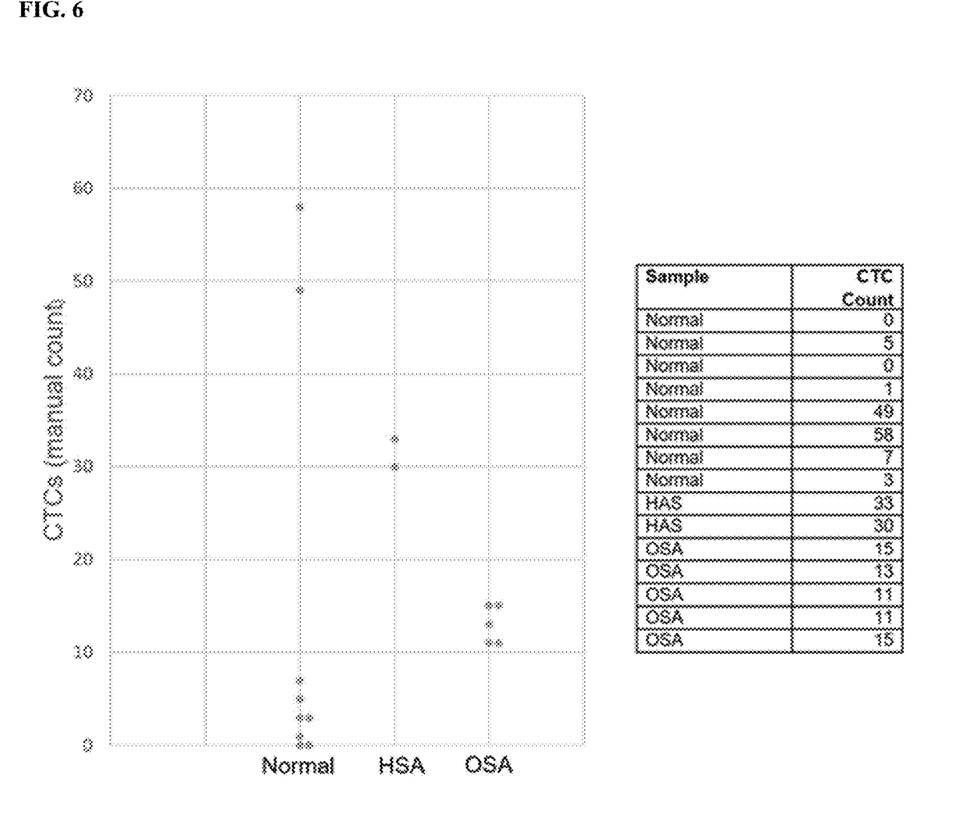
FIG. 6 shows CTC counts from clinical samples using an exemplary assay described herein, in which the cancer marker is cell-surface vimentin and the WBC marker is CD45.

After the development described above, an assay that reliably detected differences between CTC counts in normal dogs and dogs diagnosed with malignant cancer was identified (FIGS. 5 and 6). The Table below summarizes exemplary assay parameters.

| | Celsee Published Human Assay | Canine Assay |
| --- | --- | --- |
| Blood Volume | 2 mLs Human blood | 2 mLs Dog blood |
| Prefixation | 0.4% PFA | 0.4% PFA |
| Dilution | 2 mLs of Dilution Buffer (Phosphate-buffered Saline) | 2 mLs of Dilution Wash Buffer (Hank's Buffered Saline Solution + Bovine Serum Albumin) |

|  | Celsee Published Human Assay | Canine Assay |
|---|---|---|
| Fixation | 4% PFA | 4% PFA |
| Permeabilization | 0.1% Triton | 0.1% Triton |
| WBC marker | Mouse anti CD45 IgG2a (Clone F10-89-4) diluted 1:200 in 1 mL PBS | Alexa 647-Rat anti CD45 (Clone YKIX716.13) diluted 1:10 in 1 mL PBS |
| Cancer marker | Mouse anti panCK IgG1 (Clone C11) diluted 1:200 in 1 mL PBS | FITC-Mouse anti cell-surface vimentin (Clone 84-1) diluted 1:100 in 1 mL PBS |
| WBC Secondary antibody | Alexa 647 anti-msIgG2a at 1:600 | N/A |
| Cancer marker secondary antibody | Alexa 488 anti-msIgG1 at 1:600 | N/A |

REFERENCES

Gogoi P, Sepehri S, Zhou Y, Gorin M A, Paolillo C, Capoluongo E, et al. Development of an Automated and Sensitive Microfluidic Device for Capturing and Characterizing Circulating Tumor Cells (CTCs) from Clinical Blood Samples. PLoS ONE 11(1) 2016: e0147400. doi: 10.1371/journal.pone.0147400

Cobbold S and S Metcalfe. Monoclonal antibodies that define canine homologues of human CD antigens: Summary of the First International Canine Leukocyte Antigen Workshop (CLAW). Tissue Antigens, 43: 137-154. (1994), doi:10.1111/j.1399-0039.1994.tb02315.x Goto-Koshino Y, H Tomiyasu, H Suzuki, T Tamamoto, N Mizutani, Y Fujino, K Ohno, H Tsujimoto. Differential expression of CD45 isoforms in canine leukocytes. Veterinary Immunology and Immunopathology, Volume 160, Issues 1-2, Pages 118-122, 2014, doi: 10.1016/j.vetimm.2014.03.011.

Caniatti M, P Roccabianca, E Scanziani, S Paltrinieri, P F Moore. Canine Lymphoma: Immunocytochemical Analysis of Fine-needle Aspiration Biopsy. Veterinary Pathology Vol 33, Issue 2, pp. 204-212 Mar. 1, 1996. Doi: 10.1177/030098589603300210.

González-Fernandez L, C Ortega-Ferrusola, B Macias-Garcia, G M Salido, F J Pena, J A Tapia. Identification of Protein Tyrosine Phosphatases and Dual-Specificity Phosphatases in Mammalian Spermatozoa and Their Role in Sperm Motility and Protein Tyrosine Phosphorylation. Biology of Reproduction, Volume 80, Issue 6, 1 Jun. 2009, Pages 1239-1252, doi:10.1095/biolreprod.108.073486

Danilenko, D M, P F Moore and P V Rossitto. Canine leukocyte cell adhesion molecules (LeuCAMs): Characterization of the CD11/CD18 family. Tissue Antigens, 40: 13-21 (1992). doi:10.1111/j.1399-0039.1992.tb01952.x Rüigen, B C, R König, S E Hammer, S Groiss, A Saalmüller and I Schwendenwein. Composition of lymphocyte subpopulations in normal canine lymph nodes. Vet Clin Pathol, 44: 58-69 (2015). doi:10.1111/vcp.12221

N Lynn Henry and D F Hayes, Cancer biomarkers, Molecular Oncology, Volume 6, Issue 2, 2012, Pages 140-146, doi:10.1016/j.molonc.2012.01.010.

Singh A & J Settleman. EMT, cancer stem cells and drug resistance: an emerging axis of evil in the war on cancer. Oncogene volume 29, (26 Aug. 2010) pages 4741-4751. doi:10.1038/onc.2010.215

Pantel K & Alix-Panabiè C. Liquid biopsy: Potential and challenges, Molecular Oncology, 10 2016. doi: 10.1016/j.molonc.2016.01.009.

W J Allard, J Matera, M C Miller, M Repollet, M C Connelly, C Rao, A G J Tibbe, J W Uhr and L W M M Terstappen. Tumor Cells Circulate in the Peripheral Blood of All Major Carcinomas but not in Healthy Subjects or Patients With Nonmalignant Diseases. Clin Cancer Res Oct. 15, 2004 (10) (20) 6897-6904; DOI:10.1158/1078-0432.CCR-04-0378

Che J, Yu V, Dhar M, et al. Classification of large circulating tumor cells isolated with ultra-high throughput microfluidic Vortex technology. Oncotarget. 2016; 7(11):12748-12760. doi: 10.18632/oncotarget. 7220.

W Harb, A Fan, T Tran, D C Danila, D Keys, M Schwartz and C Ionescu-Zanetti. Mutational Analysis of Circulating Tumor Cells Using a Novel Microfluidic Collection Device and qPCR Assay. Translational Oncology (2013) 6, 528-538. doi: 10.1593/tlo.13367 Mikolajczyk S D, L S Millar, P Tsinberg, et al. Detection of EpCAM-Negative and Cytokeratin-Negative Circulating Tumor Cells in Peripheral Blood. Journal of Oncology, vol. 2011, Article ID 252361, 10 pages, 2011. doi:10.1155/2011/252361

Chudasama, D., N Burnside, J Beeson, E Karteris, A Rice, V Anikin. Perioperative detection of circulating tumour cells in patients with lung cancer. Oncology Letters 14.2 (2017): 1281-1286. doi:10.3892/ol.2017.6366

Chen J-Y, Tsai W-S, Shao H-J, Wu J-C, Lai J-M, Lu S-H, et al. Sensitive and Specific Biomimetic Lipid Coated Microfluidics to Isolate Viable Circulating Tumor Cells and Microemboli for Cancer Detection. PLoS ONE 11(3) (2016): e0149633. doi:10.1371/journal.pone.0149633

Adams D, S Stuart, R Martin, K Alpaugh, M Charpentier, S Tsai, R C Bergan, I M Ogden, W Catalona, S Chumsri, C-M Tang, M Cristofanilli Circulating giant macrophages as a potential biomarker of solid tumors. Proceedings of the National Academy of Sciences March 2014, 111 (9) 3514-3519; DOI:10.1073/pnas.1320198111 da Costa, A, J T Oliveira, F Gartner, B Kohn, A D Gruber, and R Klopfleisch. Potential markers for detection of circulating canine mammary tumor cells in the peripheral blood. The Veterinary Journal 190, no. 1 (2011): 165-168. doi:10.1016/j.tvjl.2010.09.027.

da Costa, A, D Lenze, M Hummel, B Kohn, A D Gruber, and R Klopfleisch. Identification of six potential markers for the detection of circulating canine mammary tumour cells in the peripheral blood identified by microarray analysis. Journal of comparative pathology 146, no. 2-3 (2012): 143-151. doi:10.1016/j.jcpa.2011.06.004.

Da Costa, A, B Kohn, A D Gruber, and R Klopfleisch. Multiple RT-PCR markers for the detection of circulating tumour cells of metastatic canine mammary tumours. The Veterinary Journal 196, no. 1 (2013): 34-39. doi:10.1016/j.tvj1.2012.08.021 Gelain, M E, V Martini, M Giantin, A Arica, A Poggi, L Aresu, F Riondato, M Dacasto, and S Comazzi. CD44 in canine leukemia: Analysis of mRNA and protein expression in peripheral blood. Veterinary immunology and immunopathology 159, no. 1-2 (2014): 91-96. doi:10.1016/j.vetimm.2014.02.008.

Meyer, A., and R. Klopfleisch. "Multiple polymerase chain reaction markers for the differentiation of canine cutaneous peripheral nerve sheath tumours versus canine fibrosarcomas." Journal of comparative pathology 150.2-3 (2014): 198-203. doi: 10.1016/j.jcpa.2013.08.006

Leader, M, M Collins, J Patel and K Henry., Vimentin: an evaluation of its role as a tumour marker. Histopathology, (1987) 11: 63-72. doi:10.1111/j.1365-2559.1987.tb02609.x Lee, J M, S Dedhar, R Kalluri, and E W Thompson. The epithelial-mesenchymal transition: new insights in signaling, development, and disease. J Cell biol 172, no. 7 (2006): 973-981. doi:10.1083/jcb.200601018

All publications, patents, patent applications and accession numbers mentioned in the above specification are herein incorporated by reference in their entirety. Although the disclosure has been described in connection with specific embodiments, it should be understood that the disclosure as claimed should not be unduly limited to such specific embodiments. Indeed, various modifications and variations of the described compositions and methods of the disclosure will be apparent to those of ordinary skill in the art and are intended to be within the scope of the following claims.

We claim:

1. An essay method of identifying the presence of cancer cells in a blood sample from a canine, comprising:
    a) preparing a canine blood sample using a method comprising the steps of i) pre-fixing said sample in approximately 0.1 to 0.8% paraformaldehyde (PFA); ii) diluting said pre-fixed sample in a buffer comprising Hank's buffered saline solution and bovine serum albumin; iii) fixing said diluted sample in 2 to 5% PFA; and iv) permeabilizing said fixed sample with 0.05 to 0.2% Triton to generate a prepared sample;
    b) isolating and capturing circulating tumor cells (CTC) from said prepared biological sample; and
    c) detecting the presence of a cell surface vimentin (Vim) polypeptide on said captured CTCs.

2. The method of claim 1, wherein said isolating and capturing said CTCs is performed on a microfluidic chip.

3. The method of claim 1, wherein said detecting CTCs expressing cell surface Vim polypeptide comprises the use of antibodies that specifically bind to said cell surface Vim polypeptide.

4. The method of claim 3, wherein said cell surface Vim polypeptide antibodies are labeled with a detectable label.

5. The method of claim 3, wherein detecting said detectably labeled Vim polypeptide antibody-bound captured CTCs is performed in said microfluidic chip.

6. The method of claim 3, wherein a volume of 1 ml of said Vim polypeptide antibodies is used.

7. The method of claim 1, wherein said method further comprises detecting the presence of captured white blood cells (WBCs).

8. The method of claim 1, wherein said pre-fixing said sample is in 0.4% PFA, said fixing is in 4% PFA, and said permeabilizing is in 0.1% Triton.

9. The method of claim 1, wherein said WBCs are identified by detecting the presence of a CD45 polypeptide on said captured WBC.

10. The method of claim 1, wherein said cancer cells are derived from one or more cancers selected from the group consisting of hemangiosarcoma, osteosarcoma, mammary cancers, mixed cancer tumors, and carcinomas.

11. The method of claim 10, wherein said assay method identifies the presence of any one of said cancers.

12. The method of claim 1, wherein a volume of 1 to 4 ml of said blood sample is used.

13. The method of claim 12, wherein a volume of 2 ml of said blood sample is used.

14. The method of claim 1, wherein said isolating and detecting said CTCs are automated.

* * * * *